United States Patent [19]
Wang et al.

[11] Patent Number: 5,952,433
[45] Date of Patent: Sep. 14, 1999

[54] MODIFIED POLYACTIDE COMPOSITIONS AND A REACTIVE-EXTRUSION PROCESS TO MAKE THE SAME

[75] Inventors: James Hongxue Wang, Appleton, Wis.; David Michael Schertz, Atlanta, Ga.

[73] Assignee: Kimberly-Clark Worldwide, Inc., Neenah, Wis.

[21] Appl. No.: 08/903,864

[22] Filed: Jul. 31, 1997

[51] Int. Cl.$^6$ ...................................................... C08L 61/00
[52] U.S. Cl. ........................................... 525/415; 528/354
[58] Field of Search ............................... 525/415; 528/354

[56] References Cited

U.S. PATENT DOCUMENTS

| | | |
|---|---|---|
| 3,806,495 | 4/1974 | Schoen . |
| 4,504,635 | 3/1985 | Weber, Jr. et al. . |
| 4,526,938 | 7/1985 | Churchill et al. . |
| 4,683,287 | 7/1987 | Koleske et al. . |
| 4,701,483 | 10/1987 | Okitsu . |
| 4,745,160 | 5/1988 | Churchill et al. . |
| 4,767,829 | 8/1988 | Kordomenos et al. . |
| 4,826,945 | 5/1989 | Cohn et al. . |
| 5,136,017 | 8/1992 | Kharas et al. . |
| 5,278,202 | 1/1994 | Dunn et al. . |
| 5,300,576 | 4/1994 | Nemphos et al. . |
| 5,322,925 | 6/1994 | Muth et al. . |
| 5,360,892 | 11/1994 | Bonsignore et al. . |
| 5,410,016 | 4/1995 | Hubbell et al. ........................... 528/354 |
| 5,417,983 | 5/1995 | Nagase et al. . |
| 5,434,241 | 7/1995 | Kim et al. . |
| 5,470,944 | 11/1995 | Bonsignore . |
| 5,472,518 | 12/1995 | Patnode et al. ........................... 428/288 |
| 5,525,671 | 6/1996 | Ebato et al. . |
| 5,567,435 | 10/1996 | Hubbell et al. . |
| 5,567,510 | 10/1996 | Patnode et al. ........................... 134/34 |
| 5,574,129 | 11/1996 | Miyoshi et al. . |
| 5,612,052 | 3/1997 | Shalaby . |

FOREIGN PATENT DOCUMENTS

| | | |
|---|---|---|
| 0 704 470 A2 | 4/1996 | European Pat. Off. . |
| 6-298921 | 10/1994 | Japan . |
| 8-239457 | 9/1996 | Japan . |

*Primary Examiner*—Edward J. Cain
*Attorney, Agent, or Firm*—Jones & Askew, LLP

[57] ABSTRACT

The present invention is a hydrolytically modified, biodegradable polymer and a method of hydrolytically modifying a biodegradable polymer. In a preferred embodiment, the invention is a method of grafting polar groups onto polylactides and modified polyactide compositions produced by the method. The polymer compositions are useful as components in flushable and degradable articles.

24 Claims, 1 Drawing Sheet

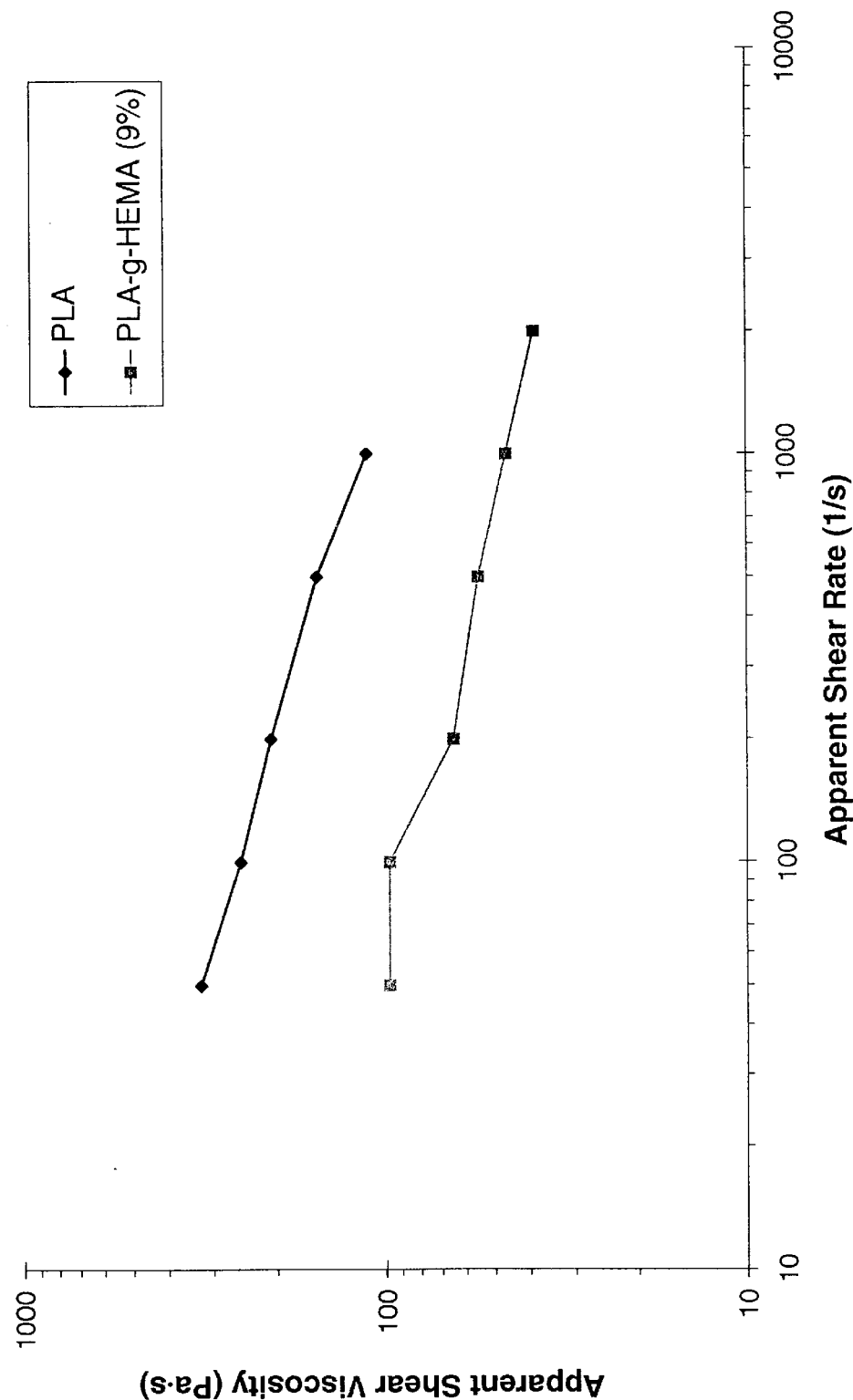

MODIFIED POLYACTIDE COMPOSITIONS AND A REACTIVE-EXTRUSION PROCESS TO MAKE THE SAME

FIELD OF THE INVENTION

The present invention relates to hydrolytically modified, biodegradable polymers and methods of hydrolytically modifying biodegradable polymer. More particularly, the present invention relates to a modified polylactide composition and a process of modifying polylactides. In a preferred embodiment, the invention relates to a method of grafting polar groups onto polylactides and grafted polylactide compositions produced by the method.

BACKGROUND OF THE INVENTION

Even though the amount of plastics, hereinafter polymers, used in a variety of consumer goods, packaging and medical articles has not significantly increased over the past twenty years, the common perception is that more and more non-degradable plastics are filling up our limited landfill space. Despite this perceived disadvantage, polymers continue to be used in the manufacture of consumer goods, packaging and medical articles because plastics offer many advantages over the more traditional materials: wood, glass, paper, and metal. The advantages of using polymers include decreased manufacturing time and costs, improved mechanical and chemical properties, and decreased weight and transportation costs. It is the improved chemical resistance properties of the majority of plastics that result in their non-degradability.

Disposal of waste materials, including food waste, packaging materials and medical waste, into a typical landfill provides a relatively stable environment in which none of these materials is seen to decompose at an appreciable rate. Alternative waste disposal options have been increasingly discussed and utilized to divert some fractions of waste from entombment. Examples of these alternatives include municipal solid waste composting, anaerobic digestion, enzymatic digestion, and waste water sewage treatment.

Much controversy is associated with the disposal of medical waste. Both government agencies and members of the private sector have been increasingly directing in-depth scrutiny and funds toward this subject. Admittedly, concerns over the fate of materials contaminated with infectious substances are valid and proper measures to insure the safety of health care workers and the general public should be taken.

Currently, medical waste can be categorized as either reusable and disposable. Categorization as to whether certain waste is reusable or disposable is customarily determined according to the material from which the article was constructed and the purpose for which the article was used.

After use, reusable medical articles are cleansed and sterilized under stringent conditions to ensure disinfection. In comparison, disposable medical articles are usually only used once. Even then, disposing procedures are not straightforward, rather they often involve several steps to safeguard against potential hazards. Typically, after use, disposable medical articles must be disinfected or sterilized, adding a significant cost prior to disposal into a specially designated landfill or waste incinerator. As a result, the disposal cost for the contaminated single use articles is quite high.

Despite the high cost of disposal, single use medical articles are desirable because of the assurance of clean, and uncontaminated equipment. Many times in the medical context, sterilization procedures conducted improperly can result in detrimental effects such as the transmission of infectious agents from one patient to another. Improper sterilization can also be disastrous in a laboratory setting, where, for example, contaminated equipment can ruin experiments resulting in tremendous costs of time and money.

Currently, disposable medical fabrics are generally composed of thermoplastic fibers such as polyethylene, polypropylene, polyesters, polyamides and acrylics. These fabrics can also include mixtures of thermoset fibers such as polyamides, polyarimides and cellulosics. They are typically 10–100 grams per square yard in weight and can be woven, knitted or otherwise formed by methods well known to those in the textile arts while the non-wovens can be thermobonded, hydroentangled, wet laid or needle punched and films can be formed by blow or cast extrusion or by solution casting. Once used, these fabrics are difficult and costly to dispose of and are non-degradable.

The use of polymers for various disposable articles is widespread and well known in the art. In fact, the heaviest use of polymers in the form of film and fibers occurs in the packaging and the disposable article industries. Films employed in the packaging industry include those used in food and non-food packaging, merchandise bags and trash bags. In the disposable article industry, the general uses of polymers occurs in the construction of diapers, personal hygiene articles, surgical drapes and hospital gowns, instrument pads, bandages, and protective covers for various articles.

In light of depleting landfill space and inadequate disposal sites, there is a need for polymers which are water-responsive. Currently, although polymers such as polyethylene, polypropylene, polyethylene terephthalate, nylon, polystyrene, polyvinyl chloride and polyvinyldene chloride are popular for their superior extrusion and film and fiber making properties, these polymers are not water-responsive. Furthermore, these polymers are generally non-compostable, which is undesirable from an environmental perspective.

Polymers and polymer blends have been developed which are generally considered to be water-responsive. These are polymers which purportedly have adequate properties to permit them to breakdown when exposed to conditions which lead to composting. Examples of such arguably water-responsive polymers include those made from starch biopolymers and polyvinyl alcohol.

Although materials made from these polymers have been employed in film and fiber containing articles, many problems have been encountered with their use. Often the polymers and articles made from these polymers are not completely water-responsive or compostable. Furthermore, some water-responsive polymers may also be unduly sensitive to water, either limiting the use of the polymer or requiring some type of surface treatment to the polymer, often rendering the polymer non water-responsive. Other polymers are undesirable because they have inadequate heat resistance for wide spread use.

Personal care products, such as diapers, sanitary napkins, adult incontinence garments, and the like are generally constructed from a number of different components and materials. Such articles usually have some component, usually the backing layer, constructed of a liquid repellent or water-barrier polymer material. The water-barrier material commonly used includes polymer materials such as polyethylene film or copolymers of ethylene and other polar and nonpolar monomers. The purpose of the water-barrier layer is to minimize or prevent absorbed liquid that may, during use, exude from the absorbent component and soil the user or adjacent clothing. The water-barrier layer also has the advantage of allowing greater utilization of the absorbent capacity of the product.

Although such products are relatively inexpensive, sanitary and easy to use, disposal of a soiled product is not without its problems. Typically, the soiled products are disposed in a solid waste receptacle. This adds to solid waste disposal accumulation and costs and presents health risks to persons who may come in contact with the soiled product. An ideal disposal alternative would be to use municipal sewage treatment and private residential septic systems by flushing the soiled product in a toilet. Products suited for disposal in sewage systems are termed "flushable". While flushing such articles would be convenient, prior art materials do not disintegrate in water. This tends to plug toilets and sewer pipes, frequently necessitating a visit from a plumber. At the municipal sewage treatment plant, the liquid repellent material may disrupt operations by plugging screens and causing sewage disposal problems. It therefore is necessary, although undesirable, to separate the barrier film material from the absorbent article prior to flushing.

In addition to the article itself, typically the packaging in which the disposable article is distributed is also made from a water-barrier, specifically water-resistant, material.

Water-resistivity is necessary to prevent the degradation of the packaging from environmental conditions and to protect the disposable articles therein. Although this packaging may be safely stored with other refuse for commercial disposal, and especially in the case of individual packaging of the products, it would be more convenient to dispose of the packaging in the toilet with the discarded, disposable article. However, where such packaging is composed of a water-resistant material, the aforementioned problems persist.

The use of lactic acid and lactide to manufacture a water-stable polymer is well known in the medical industry. Such polymers have been used in the past for making water-stable sutures, clamps, bone plates and biologically active controlled release devices. Processes developed for the manufacture of such polymers to be utilized in the medical industry have incorporated techniques which respond to the need for high purity and biocompatability in the final product. These processes, however, are typically designed to produce small volumes of high dollar-value products, with less emphasis on manufacturing cost and yield.

It is generally known that lactide polymers or poly (lactides) are unstable. However, the consequence of this instability has several aspects. One aspect is the biodegradation or other forms of degradation which occur when lactide polymers, or articles manufactured from lactide polymers, are discarded or composted after completing their useful life. Another aspect of such instability is the degradation of lactide polymers during processing at elevated temperatures as, for example, during melt-processing by end-user purchasers of polymer resins.

In the medical area there is a predominant need for polymers which are highly stable and therefore desirable for use in medical devices. Such a demand has historically been prevalent in the high value, low volume medical specialty market, but is now also equally prevalent in the low value, high volume medical market.

As described in U.S. Pat. No. 5,472,518, compositions comprised of multilayer polymer films are known in the art. The utility of such structures lies in the manipulation of physical properties in order to increase the stability or lifetime during use of such structure. For example U.S. Pat. No. 4,826,493 describes the use of a thin layer of hydroxybutyrate polymer as a component of a multilayer structure as a barrier film for diaper components and ostomy bags.

Another example of use of multilayer films is found in U.S. Pat. No. 4,620,999 which describes the use of a water soluble film coated with, or laminated to, a water insoluble film as a disposable bag. The patent describes a package for body waste which is stable to human waste during use, but which can be made to degrade in the toilet, at a rate suitable for entry into a sewage system without blockage, by adding a caustic substance to achieve a pH level of at least 12. Such structures are usually consist of a polyvinyl alcohol film layer coated with polyhydroxybutryate.

A similar excretion-treating bag allowing discarding in flush toilet or sludge vessel is disclosed in JP 61-42127. It is composed of an inner layer of water-resistant water-dispersible resin such as polylactide and an outer layer of polyvinyl alcohol. As disclosed in this patent, there are many examples of multilayer films that are utilized in disposable objects. Most of these examples consist of films or fibers which are comprised of external layers of an environmentally degradable polymer and an internal layer of water-responsive polymer. Typically, the external layers are comprised of polycaprolactone or ethylene vinyl acetate and the internal layer is comprised of polyvinyl alcohol. These examples, however, are all limited to compositions consisting of multilayers of different polymers, and do not encompass actual blends of different polymers.

A family of patents, EP 241178, JP 62-223112 and U.S. Pat. No. 4,933,182, describes a controlled release composition for treating periodontal disease. The controlled release compositions are comprised of a therapeutically effective agent in a carrier consisting of particles of a polymer of limited water solubility dispersed in a water soluble polymer. Although, the carrier of these inventions includes the use of more than one polymer, the disclosed carrier is not a blend because the water soluble polymer of limited solubility is incorporated in the water soluble polymer as particles ranging in average particle size from 1 to 500 microns.

The use of polymers for use in water-responsive articles is disclosed in U.S. Pat. No. 5,508,101, U.S. Pat. No. 5,567,510, and U.S. Pat. No. 5,472,518. This group of patents discloses a series of water-responsive compositions comprising a hydrolytically degradable polymer and a water soluble polymer. The compositions of this group, however, consist of articles constructed from polymers which are first formed into fibers or films and then combined. As such, the compositions are actually mini-layers of the individual polymer films or fibers. Therefore, although the fibers and films of the polymers of such compositions are considered to be in very close proximity with one another, they are not actual blends. The dispersion of one polymer within another in these compositions, is not viewed as approximately uniform since the individual polymers are essentially distinct and separate fibers or films.

U.S. Pat. No. 5,525,671 to Ebato et al. discloses a method of making a linear lactide copolymer from a lactide monomer and a hydroxyl group containing monomer. The polymer disclosed by Ebato is a linear lactide copolymer produced by reacting two monomers to form a linear polymer with a block or random structure. Ebato does not disclose graft copolymers.

Polymer blend compositions for making fibers and films that are optimally combined are desirable because they are highly stable. Optimal combination of polymers means that the polymers are connected as closely as possible without the requirement of co-polymerization. Although blended polymer compositions are known, improved polymer blends wherein the fibers and films are more intimately connected are desirable since the resulting composition is then more stable, pliable and versatile.

In addition to the need for polymer compositions that are highly stable, and therefore, suitable for regular use in most disposable articles, there is a simultaneous need for such polymer compositions to be water-responsive. What is needed therefore, is a material that may be utilized for the manufacture of disposable articles and which is water-responsive. Such material should be versatile and inexpensive to produce. The material should be stable enough for intended use but subject to degradation under predetermined conditions.

Moreover, there is an increased emphasis on environmentally safe materials and coatings. These coatings reduce the use of solvent-based coatings and rely, to an ever increasing degree, on polar coatings, such as water-based material. The utility of the graft copolymers of this invention includes, but would not be limited to, materials have a greater affinity for a polar coating.

Therefore, it is an object of this invention to make a hydrolytically modified, biodegradable polymer.

Another object of this invention is to make a thermally processable polymer.

Another object of this invention is to make a commercially viable polymer.

Another object of this invention is to make a thermally processable, biodegradable polymer which is more compatible with polar polymers and other polar substrates.

Another object of this invention is to make a hydrolytically modified, biodegradable polymer useful for making flushable, biodegradable articles.

Another object of this invention is to make a hydrolytically modified, biodegradable polymer useful for making blends with improved mechanical and physical properties.

Another object of this invention is to make a modified polylactide which has improved compatibility in blends with polar polymers.

Another object of the invention is to make improved blends comprising polylactides.

SUMMARY OF THE INVENTION

This invention discloses modified polylactide compositions comprised of polylactide grafted with polar monomers. This invention describes compositions of polylactide grafted with 2-hydroxyethyl methacrylate or poly(ethylene glycol) methacrylate and a reactive extrusion process for making modified polylactide compositions.

Polylactides are biodegradable polymers which are commercially viable and thermally processable. By grafting polar monomers onto a polylactide, the resulting modified polylactide is more compatible with polar polymers and other polar substrates. For flushable material development, the modified polylactide compositions of this invention have enhanced compatibility with water-soluble polymers such as polyvinyl alcohol and polyethylene oxide, than unmodified polylactide. The compatibility of modified polylactide compositions with a polar material can be controlled by the selection of the monomer and the level of grafting. Tailoring the compatibility of blends with modified polylactide compositions leads to better processability and improved physical properties of the resulting blend.

The water-responsive compositions disclosed in this invention have the unique advantage of being biodegradable so that the compositions and articles made from the compositions can be degraded in aeration tanks by aerobic degradation and anaerobic digestors by anaerobic degradation in waste water treatment plants. Therefore, articles made from the compositions of this invention will not significantly increase the volume of sludge accumulated at waste water treatment plants.

BRIEF DESCRIPTION OF THE FIGURES

FIG. 1 is a plot of the viscosity versus the shear rate of a grafted polylactide in accordance with the present invention and an ungrafted polylactide, demonstrating the decrease in viscosity of grafted polylactide versus ungrafted polylactide.

DETAILED DESCRIPTION OF THE INVENTION

Polylactide (PLA) resins are produced by different synthetic methods, such as ring-opening polymerization of lactide or direct condensation polymerization from lactic acid. Both methods of polymerization are useful for this invention. PLA is a biodegradable polymer and has the chemical structure:

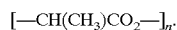
$[-CH(CH_3)CO_2-]_n$.

The PLA compositions described in the following Examples were made by using a reagent grade PLA purchased from Aldrich Chemical Company of Milwaukee, Wis. (Aldrich Catalog number 42,232-6). The PLA purchased from Aldrich Chemical Company is biodegradable and has number-average molecular weight of approximately 60,000 and a weight-average molecular weight of approximately 144,000. This PLA is made up primarily of the L-isomer and has a glass transition temperature ($T_g$) of 60° C. Any PLA can be selected for use in this invention, and the molecular weights of the PLA may vary depending on the desired properties and use.

Ethylenically unsaturated monomers containing a polar functional group, such as hydroxyl, carboxyl, amino, carbonyl, halo, thiol, sulfonic, sulfonate, etc. are appropriate for this invention. Preferred ethylenically unsaturated monomers containing a polar functional group include 2-hydroxyethyl methacrylate (HEMA) and poly(ethylene glycol) methacrylate (PEG-MA). It is expected that a wide range of polar vinyl monomers would be capable of imparting the same effects as HEMA and PEG-MA to polylactide resins and would be effective monomers for grafting. The grafted PLA may contain from 1 to 20% of grafted polar monomers, oligomers, or polymers, Preferably, the grafted PLA contains 2.5 to 20% of grafted polar monomers, oligomers, or polymers, and most preferably 2.5 to 10% of grafted polar monomers, oligomers, or polymers.

Both the HEMA (Aldrich Catalog number 12,863-8) and the PEG-MA (Aldrich Catalog number 40,954-5) used in the Examples were supplied by Aldrich Chemical Company. The PEG-MA purchased from Aldrich Chemical Company was poly(ethylene glycol) ethyl ether methacrylate having a number average molecular weight of approximately 246 grams per mol.

The method for making the grafted polylactide compositions has been demonstrated by a reactive-extrusion process. The grafting reaction can also be performed in other reaction devices as long as the necessary mixing of PLA and HEMA and/or PEG-MA and any other reactive ingredients is achieved and enough energy is provided to effect the grafting reactions.

Other reactive ingredients which may be added to the compositions of this invention include initiators such as Lupersol 101, a liquid, organic peroxide available from Elf Atochem North America, Inc. of Philadelphia, Pa. Free radical initiators useful in the practice of this invention include acyl peroxides such as benzoyl peroxide; dialkyl; diaryl; or aralkyl peroxides such as di-t-butyl peroxide; dicumyl peroxide; cumyl butyl peroxide; 1,1 di-t-butyl peroxy-3,5,5-trimethylcyclohexane; 2,5-dimethyl-2,5-di (tbutylperoxy) hexane; 2,5-dimethyl-2,5-bis (t-butylperoxy) hexyne-3 and bis(a-t-butyl peroxyisopropylbenzene); peroxyesters such as t-butyl peroxypivalate; t-butyl peroctoate; t-butyl perbenzoate; 2,5-dimethylhexyl-2,5-di(perbenzoate) t-butyl di(perphthalate); dialkyl peroxymonocarbonates and peroxydicarbonates; hydroperoxides such as t-butyl hydroperoxide, p-methane hydroperoxide, pinane hydroperoxide and cumene hydroperoxide and ketone peroxides such cyclohexanone peroxide and methyl ethyl ketone peroxide. Azo compounds such as azobisisobutyronitrile may also be used.

Furthermore, other components known in the art may be added to the graft polymers of this invention to further enhance the properties of the final material. For example, polyethylene glycol may be further added to improve melt viscosity. Additives of other types may also be incorporated to provide specific properties as desired. For example, anti-static agents, pigments, colorants and the like may be incorporated in to the polymer composition. Additionally, processing characteristics may be improved by incorporating lubricants or slip agents into blends made from polymers of the invention. All of these additives are generally used in relatively small amounts, usually less than 3 weight percent of the final composition.

The mixture of the polylactide and the polar monomer, oligomer, or polymer is subjected to mechanical deformation in a suitable mixing device, such as a Bradender Plasticorder, a roll mill, a single or multiple screw extruder, or any other mechanical mixing device which can be used to mix, compound, process or fabricate polymers. A particularly desirable reaction device is an extruder having one or more ports. In a preferred embodiment, the reaction device is a co-rotating, twin-screw extruder, such as a ZSK-30 twin-screw compounding extruder manufactured by Werner & Pfleiderer Corporation of Ramsey, N.J. This extruder allows multiple feeding and venting ports.

The presence of PLA or modified PLA in blends used to make fibers, films or other shapes reduces the water sensitivity of pure PVOH in use. PLA grafted with a polar monomer or a mixture of monomers is preferred for enhanced compatibility with PVOH in order to obtain superior processing and mechanical and physical properties. It is possible to use the blends to make other shapes than fibers or films and to thermally form the blends into complex shapes.

As used herein, the term "water-dispersible" means that the composition dissolves or breaks into pieces smaller than a 20 mesh after being immersed in water for approximately five minutes. The term "water-disintegratable" means that the composition breaks into multiple pieces within five minutes of immersion in water and that some of the pieces will be caught by a 20 mesh screen without slipping through in the same manner as a thread through the eye of a needle. The term "water-weakenable" means that the composition remains in one piece but weakens and loses rigidity after five minutes of immersion in water and becomes drapeable, i.e. it bends without an external force applied thereto when it is held by one side at a horizontal position. The term "water-stable" means that the composition does not become drapeable after five minutes of immersion in water and remains in one piece after the water response test.

As used herein, the term "graft copolymer" means a copolymer produced by the combination of two or more chains of constitutionally or configurationally different features, one of which serves as a backbone main chain, and at least one of which is bonded at some point(s) along the backbone and constitutes a side chain. The molar amount of grafted monomer, oligomer or polymer, i.e. side-chain species, may vary but should be greater than molar amount of the parent species. The term "grafted" means a copolymer has been created which comprises side chains or species bonded at some point(s) along the backbone of a parent polymer. The term "blend" as applied to polymers means an intimate combination of two or more polymer chains of constitutionally or configurationally different features which are not bonded to each other. Such blends may be homogenous or heterogeneous. (See Sperling, L. H., *Introduction to Physical Polymer Science* 1986 pp. 44–47 which is herein incorporated by reference in its entirety.) Preferably, the blend is created by combining two or more polymers at a temperature above the melting point of each polymer.

The present invention is illustrated in greater detail by the following specific Examples. It is to be understood that these Examples are illustrative embodiments and that this invention is not to be limited by any of the Examples or details in the description. Rather, the claims appended hereto are to be construed broadly within the scope and spirit of the invention.

EXAMPLES

Example 1

Reactive-Extrusion of Polylactide with HEMA

A co-rotating, twin-screw extruder, ZSK-30 manufactured by Werner & Pfleiderer Corporation of Ramsey, N.J. was used to manufacture the modified PLA of the Examples. The diameter of the extruder was 30 mm. The length of the screws was 1388 mm. This extruder had 14 barrels, numbered consecutively 1 to 14 from the feed hopper to the die. The first barrel, barrel #1, received the PLA and was not heated but cooled by water. The vinyl monomer, HEMA, was injected into barrel #5 and the Lupersol 101 peroxide by Atochem was injected into barrel #6. Both the monomer and the peroxide were injected via a pressurized nozzle injector. A vacuum port for devolatilization was included at barrel #11. The die used to extrude the modified PLA strands had four openings of 3 mm in diameter which were separated by 7 mm. The modified PLA strands were then cooled in a cold water bath and then pelletized.

The PLA was fed into the extruder with a volumetric feeder at a throughput of 20 lb/hr. The HEMA and the peroxide were injected into the extruder at throughputs of 1.8 lb/hr and 0.09 lb/hr, respectively. The screw speed was 300 rpm.

The following extruder barrel set temperatures were used during the extrusion run:

| Zone 1 | Zone 2 | Zone 3 | Zone 4 | Zone 5 | Zone 6 | Zone 7 |
| --- | --- | --- | --- | --- | --- | --- |
| 180° C. | 180° C. | 180° C. | 180° C. | 180° C. | 170° C. | 160° C. |

The vacuum was turned on for devolatization at barrel #11 and the process was allowed to stabilize. The extruded HEMA grafted PLA (PLA-g-HEMA) strands were cooled in a cold water bath and then pelletized.

Melt rheology tests were performed on the modified and unmodified PLA on a Goettfert Rhoegraph 2000 available from Goettfert in Rock Hill, S.C. The modified PLA of this Example was prepared with 9 weight percent HEMA and 0.45 weight percent Lupersol. The weight percentages of the HEMA and Lupersol were based on the weight of the PLA.

The melt rheology tests were performed at 180° C. with a 30/1 (length/diameter) mm/mm die. The apparent melt viscosity was determined at apparent shear rates of 50, 100, 200, 500, 1000, and 2000 l/s. A rheology curve was plotted for each material of the apparent viscosity versus the apparent shear rates below.

| Sample | PLA, Aldrich | PLA-g-HEMA (9%, 0.45%) |
| --- | --- | --- |
| Comment | Extruded Control | Grafted PLA |
| App. Shear Rate (l/s) | App. Shear Visc. (Pa s) | App. Shear Visc. (Pa s) |
| 49.997 | 325.7 | 97.71 |
| 99.994 | 252.42 | 97.71 |
| 199.99 | 207.63 | 65.14 |
| 499.97 | 154.71 | 55.369 |
| 1000 | 112.35 | 46.407 |
| 2000 | 82.235 | 38.675 |

The apparent melt viscosities at the various apparent shear rates were plotted and rheology curves for the unmodified PLA and the modified PLA of the above Example were generated as shown in FIG. 2. The rheology curve of the modified PLA demonstrates the reduced viscosities of the modified PLA when compared to the unmodified PLA. These reduced viscosities of the modified PLA result in improved processability of the PLA. The grafting of polar monomers, oligomers or polymers onto PLA results in improved compatibility with both polar materials and polar substrates.

Example 2

Fibers Made From Blends Comprising PVOH and Modified PLA or Unmodified PLA

The water-responsive fibers of the following Example are comprised of a melt blend of polyvinyl alcohol (PVOH) and either unmodified PLA or PLA as modified in Example 1. The range of the compositions for water-responsive fibers varies from 1 to 99 weight percent of unmodified or modified PLA in the blend. The modified PLA used in the blends is as described above in Example 1 and the unmodified PLA used in the blends was that as supplied by Aldrich Chemical Company. The PVOH used in the blends was Ecomaty AX10000 supplied by Nippon Gohsei, Japan and is a cold-water soluble polymer synthesized from partially hydrolyzed polyvinyl acetate and containing side chain branches. The melt flow rate of the PVOH used was 100 g/10 min. at 230° C. and 2.16 kg.

Extrusion Process for Polymer Blending

Water-responsive blend compositions were prepared by a melt extrusion process. It is preferred to blend or mix the two components in an extruder such as a twin-screw or even a single screw extruder under appropriate temperature and shear/pressure conditions. The blending process can also be performed in a batchwise mixing device, such as a melt mixer or a kneader, which is discussed in the next section. Both PVOH and unmodified or modified PLA can be fed to an extruder either simultaneously or in sequence to minimize any adverse effects on the polymers such as degradation or discoloration.

In this Example, the extrusion process of the blends was performed using a Haake TW-100, a counter-rotating, twin screw extruder. The extrusion set temperatures for the four heating zones were 170, 180, 180 and 168° C. The screw speed was 150 rpm. A resin mixture of PLA or modified PLA and PVOH was fed into the extruder at a rate of 10 lb/hr. The melt was extruded, air-cooled and then pelletized.

Extruded blend compositions which contained 20, 30, and 40 weight percent of either PLA or modified PLA of Example 1 and 80, 70, and 60 weight percent PVOH, respectively, were produced and used for fiber-spinning.

Melt Mixing Process for Polymer Blending

Water-responsive blend compositions were also prepared by a melt mixing process. In this Example, the melt mixing process was performed using a Haake Rheomix® 600, a counter-rotating, twin roller mixer. The mixer set temperature was 180° C. The screw speed was 150 rpm. 70 grams of total resin mixture was fed into the mixer and blended for five minutes. The melt was removed from the mixer and then cooled in air.

Melt mixer compositions which contained 50 and 60 weight percent of either PLA or modified PLA of Example 1 and 50 and 40 weight percent of PVOH were produced and used for fiber-spinning.

Fiber Processing of the Blends

The fibers were made on a small-scale fiber spinning processing equipment. The device consists of a vertically mounted cylinder heated by cartridge heaters. A vertically mounted Worm Gear Jactuator (Model: PKN-1801-3-1, manufactured by Duff-Northon Company, Charlotte, N.C.) was used to extrude the materials into fibers.

The fibers were spun from a spin plate with 3 openings of 0.356 mm. The fibers exiting the die were wound on a drum having both reciprocating and rotary movements to collect fiber samples.

Fibers were prepared with varying amounts of PVOH and the unmodified PLA or modified PLA of Example 1.

Example A) PLA/PVOH 20/80 weight ratio fibers.

The temperature of the cylinder was set at 360° C. At this temperature, soft fibers were made from this polymer blend which was comprised of unmodified polylactide and polymer vinyl alcohol. The fibers were slightly yellowish.

Example B) PLA-g-HEMA/PVOH 20/80 weight ratio fibers.

This sample was made from the HEMA grafted PLA and polyvinyl alcohol. The temperature of the barrel was also set at 360° C. This polymer blend was made into fibers of less color than the fibers made from the unmodified blend above. These fibers were nearly colorless. This polymer blend exhibited substantially higher melt strength than the blend containing unmodified PLA, presumably due to the improved compatibility of the HEMA grafted PLA with PVOH. As a result, the fibers could be extruded at a higher extrusion rate than those from the blends containing unmodified PLA. Fibers could be produced in a temperature range from 353 to 371° C.

Example C) PLA/PVOH 30/70 weight ratio fibers.

This blend composition was also spun into fibers. Some melt fracture occurred.

Example D) PLA-g-HEMA/PVOH 30/70 weight ratio fibers.

Soft and nearly colorless fibers were made from this blend composition. This blend showed improved processability over the unmodified PLA/PVOH 30/70 blend.

Example E) PLA/PVOH 40/60 weight ratio fibers.
Example F) PLA-g-HEMA/PVOH 40/60 weight ratio fibers.
Example G) PLA/PVOH 50/50 weight ratio, mixer blended fibers.
Example H) PLA-g-HEMA/PVOH 50/50 weight ratio, mixer blended fibers.
Example I) PLA/PVOH 60/40 weight ratio, mixer blended fibers.
Example J) PLA-g-HEMA/PVOH 60/40 weight ratio, mixer blended fibers.

The blends containing HEMA grafted PLA had lower viscosities than the blends containing unmodified PLA and thus could be extruded at higher rates and exhibited improved processability. Additionally, the fibers from the blends containing modified PLA exhibited less discoloration than fibers from the blends containing unmodified PLA, suggesting improved compatibility of the modified PLA. All of the blends containing HEMA grafted PLA exhibited higher melt strength and better fiber processability than those containing unmodified PLA blends at the same weight ratios.

Water Response Test of the HEMA grafted PLA/PVOH Fibers

For each of the above compositions, a section of the prepared fiber was cut measuring about one inch long. The diameter of the fiber was measured and recorded. The water-response test involved using a pair of tweezers to hold the section of the fiber, immersing it into a scintillation vial filled with 20 milliliters of water and holding it there for five minutes. After five minutes, the cap was placed on the scintillation vial and the vial was placed in a Model 75 Shaker (available from Burrell Corp., Pittsburgh, Pa.). The vial was shaken for 30 seconds with the shaker set at maximum speed. If the fiber began to disperse or disintegrate, the contents of the scintillation vial were emptied through a 20 mesh screen (20 mesh U.S.A. Standard Testing Sieve, ASTM E-11 Specification, No. 20). The vial was then rinsed with 20 milliliters of water from a squeeze bottle to remove any remaining fiber pieces and emptied through the sieve. If the fiber did not disperse or disintegrate, the fiber was observed for any loss in rigidity.

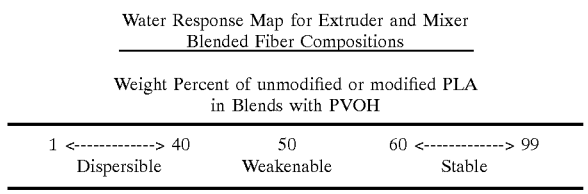

Water Response Map for Extruder and Mixer Blended Fiber Compositions

Weight Percent of unmodified or modified PLA in Blends with PVOH

1 <-------------> 40        50        60 <-------------> 99
  Dispersible        Weakenable        Stable Fibers made from blend compositions were water-dispersible up to about 40 weight percent of modified or unmodified PLA in the blend. The fibers made from blends with about 60 or greater weight percent of unmodified or modified PLA were water-stable. The fibers made from blends between these two ranges should be considered water-weakenable. The fibers made from blends with about 50 weight percent of unmodified or unmodified PLA were water-weakenable.

Example 3

Films Made From Blends Comprising PVOH and Modified PLA or Unmodified PLA

The water-responsive films of the following Examples are composed of melt blends of unmodified or modified PLA and PVOH. The range of the compositions for water-responsive films vary from 1 to 99 weight percent of unmodified or modified PLA in the blend. The presence of PLA or modified PLA in the blend used to make films reduces the water sensitivity of pure PVOH in use. PLA grafted with a polar monomer or a mixture of monomers is preferred for enhanced compatibility with PVOH in order to obtain superior mechanical and physical properties. The modified PLA used in the blends is as described above in Example 1 and the unmodified PLA used in the blends was that as supplied by Aldrich Chemical Company. The PVOH used in the blends was Ecomaty AX10000 supplied by Nippon Gohsei, Japan, a cold-water soluble polymer synthesized from partially hydrolyzed polyvinyl acetate containing side branches.

Extrusion Process for Polymer Blending

Water-responsive blend compositions were prepared by a melt extrusion process. It is preferred to blend or mix the two components in an extruder such as a twin-screw or even a single screw extruder under appropriate temperature and shear/pressure conditions. The blending process can also be performed in a batchwise mixing device, such as a melt mixer or a kneader, which is discussed in the next section. Both PVOH and modified PLA can be fed to an extruder either simultaneously or in sequence to minimize any adverse effects on the polymers such as degradation or discoloration.

In these Examples, the extrusion process of the blends was performed using a Haake TW-100, a counter-rotating, twin screw extruder. The extrusion set temperatures for the four heating zones were 170, 180, 180 and 168° C. The screw speed was 150 rpm. A resin mixture of PLA or modified PLA and PVOH was fed into the extruder at a rate of 10 lb/hr. The melt was extruded, air-cooled and then pelletized.

Extruded blend compositions which contained 20, 30, and 40 weight percent of either unmodified PLA or modified PLA and 80, 70 and 60 weight percent PVOH, respectively, were produced and used to make films in this Example.

Melt Mixing Process for Polymer Blending

Water-responsive blend compositions were also prepared by a melt mixing process. In these Examples, the melt mixing process was performed using a Haake Rheomix® 600, a counter-rotating, twin roller mixer. The mixer set temperature was 180° C. The screw speed was 150 rpm. 70 grams of total resin mixture was fed into the mixer and blended for five minutes. The melt was removed from the mixer and then cooled in air.

Melt mixer compositions containing 30, 40, 50 and 60 weight percent HEMA grafted PLA and 70, 60, 50 and 40 weight percent PVOH, respectively, were produced and used to make the films in this Example.

Film Preparation

A film was prepared for each blend composition using a Carver hot press with two heated platens at a temperature of 190° C. and a pressure of 15,000 psi for about one minute. The thickness of the films in this Example were approximately 4 mils. However, the thickness of the films could be either increased or decreased depending on the final use and properties desired.

Water Response Test of the HEMA grafted PLA/PVOH Films

For each of the compositions, a section of the prepared film was cut measuring about ¼ of an inch by about ½ of an inch. The water-response test involved using a pair of tweezers to hold the section of the film, immersing it into a scintillation vial filled with 20 milliliters of water and holding it there for five minutes. After five minutes, the cap was placed on the scintillation vial and the vial was placed in a Model 75 Shaker (available from Burrell Corp., Pittsburgh, Pa.). The vial was shaken for 30 seconds with the shaker set at maximum speed. If the film began to disperse or disintegrate, the contents of the scintillation vial were emptied through a 20 mesh screen (20 mesh U.S.A. Standard Testing Sieve, ASTM E-11 Specification, No. 20). The vial was then rinsed with 20 milliliters of water from a squeeze bottle to remove any remaining film pieces and emptied through the sieve. If the film did not disperse or disintegrate, the film was observed for any loss in rigidity.

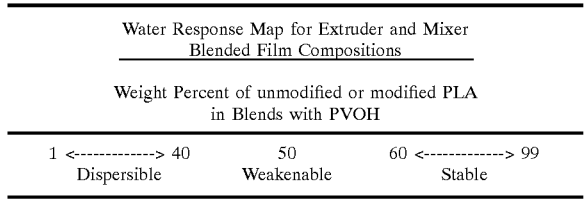

Films made from blend compositions were water-dispersible up to about 40 weight percent of modified or unmodified PLA in the blend. The films made from blends with about 60 or greater weight percent of unmodified or modified PLA were water-stable. The films made from blends between these two ranges should be considered water-weakenable. The films made from blends with about 50 weight percent of unmodified or unmodified PLA were water-weakenable.

It is to be understood that these Examples are illustrative embodiments and that this invention is not to be limited by any of the Examples or details in the description. Rather, the claims appended hereto are to be construed broadly within the scope and spirit of the invention. Particularly, it is to be understood that the invention include multilayer films and fibers or articles in which the claimed film or fiber is a layer in the final product.

We claim:

1. A polymer composition comprising a polylactide grafted with a polar monomer, oligomer, or polymer or a combination thereof.

2. The polymer composition of claim 1, wherein said polar monomer is an ethylenically unsaturated monomer containing at least one polar functional group or said oligomer or said polymer is an oligomer or a polymer polymerized from an ethylenically unsaturated monomer containing at least one polar functional group.

3. The polymer composition of claim 2, wherein said at least one polar functional group is a hydroxyl, carboxyl or sulfonate group or a combination thereof.

4. The polymer composition of claim 3, wherein said at least one polar functional group is a hydroxyl group.

5. The polymer composition of claim 1, wherein said polar monomer is a polar vinyl monomer.

6. The polymer composition of claim 1, wherein said polar monomer, oligomer, or polymer is selected from the group consisting of 2-hydroxyethyl methacrylate and polyethylene glycol methacrylate and derivatives thereof.

7. The polymer composition of claim 6, wherein said polar monomer, oligomer, or polymer is 2-hydroxyethyl methacrylate or its derivatives.

8. The polymer composition of claim 1, wherein said polylactide contains from 1 to 20 weight percent grafted polar monomer, oligomer or polymer or combination thereof.

9. The polymer composition of claim 1, wherein said polylactide is melt blended with a second polymer.

10. The polymer composition of claim 9, wherein said composition is water-dispersible, water-weakenable or water-stable.

11. A polymer composition comprising a polylactide backbone with a plurality of polar monomers, oligomers, polymers or mixture thereof grafted onto said polylactide backbone.

12. A method of making a grafted polylactide composition comprising the steps of:
   a) combining a polylactide and a polar monomer, oligomer, or polymer in a reaction vessel; and
   b) providing sufficient energy to the combination of said polylactide and said polar monomer, oligomer, or polymer in order to form said grafted polylactide composition.

13. The method of claim 12, wherein said reaction vessel is an extruder.

14. The method of claim 13, wherein said extruder is a co-rotating, twin-screw extruder.

15. The method of claim 12, wherein said polar monomer is an ethylenically unsaturated monomer containing at least one polar functional group or said oligomer or said polymer is an oligomer or a polymer polymerized from an ethylenically unsaturated monomer containing at least one polar functional group.

16. The method of claim 15, wherein said at least one polar functional group is a hydroxyl, carboxyl or sulfonate group or a combination thereof.

17. The method of claim 12, wherein said polar monomer is a polar vinyl monomer.

18. The method of claim 12, wherein said polar monomer, oligomer, or polymer is selected from the group consisting of 2-hydroxyethyl methacrylate and polyethylene glycol methacrylate and their derivatives.

19. The method of claim 12, wherein said sufficient energy is provided in the form of heat.

20. The method of claim 12, wherein an initiator is added to the mixture.

21. A polymer composition comprising a grafted polylactide, wherein the grafted polylactide is a polylactide grafted with from about 1 weight percent to about 20 weight percent of 2-hydroxyethyl methacrylate.

22. A polymer composition comprising a grafted polylactide, wherein the grafted polylactide is a polylactide grafted with from about 1 weight percent to about 20 weight percent of poly(ethylene glycol) methacrylate and its derivatives.

23. The polymer composition of claim 21 wherein the grafted polylactide is a polylactide grafted with from about 1 weight percent to about 20 weight percent of poly(ethylene glycol) ethyl ether methacrylate.

24. A method of making a polymer composition comprising the steps of:
   a) mixing a polylactide, an initiator and a monomer selected from the group consisting of 2-hydroxyethyl methacrylate, poly(ethylene glycol) methacrylate and their derivatives;
   b) providing sufficient energy in the form of heat to the mixture of the polylactide, the initiator and the monomer selected from the group consisting of 2-hydroxyethyl methacrylate, poly(ethylene glycol) methacrylate and their derivativee to graft the monomer selected from the group consisting of 2-hydroxyethyl methacrylate, poly(ethylene glycol) methacrylate and their derivatives to the polylactide.

* * * * *

UNITED STATES PATENT AND TRADEMARK OFFICE
CERTIFICATE OF CORRECTION

PATENT NO. : 5,952,433

DATED : September 14, 1999

INVENTOR(S) : Wang et al.

It is certified that error appears in the above-identified patent and that said Letters Patent is hereby corrected as shown below:

Title Page, item [54] and Column 1, line 1:

MODIFIED POLYLACTIDE COMPOSITIONS AND A REACTIVE-EXTRUSION PROCESS TO MAKE THE SAME

Signed and Sealed this

Twenty-ninth Day of February, 2000

Attest:

Q. TODD DICKINSON

Attesting Officer

Commissioner of Patents and Trademarks